US012806385B2

United States Patent
(12) Holman et al.

(10) Patent No.: US 12,806,385 B2
(45) Date of Patent: Nov. 24, 2026

(54) MEDICAL DRAIN DEVICE

(71) Applicant: PMR DEVICE, LLC, Spring Branch, TX (US)

(72) Inventors: Paul Holman, Canyon Lake, TX (US); Ryan Cantrell, Richmond, TX (US); Matthew Padron, Spring Branch, TX (US); Hunter Ricardo Adams, Corpus Christi, TX (US); Zuhair Zafir Hawa, Leawood, KS (US); Austin Hwang, Fremont, CA (US); Lilith Delan Liang, Houston, TX (US); Tate Edward Shannon, Sonora, TX (US); Zengyi Wan, Shanghai (CN)

(73) Assignee: PMR DEVICE, LLC, Spring Branch, TX (US)

(*) Notice: Subject to any disclaimer, the term of this patent is extended or adjusted under 35 U.S.C. 154(b) by 496 days.

(21) Appl. No.: 18/556,395

(22) PCT Filed: Apr. 20, 2022

(86) PCT No.: PCT/US2022/025537

§ 371 (c)(1),
(2) Date: Oct. 20, 2023

(87) PCT Pub. No.: WO2022/226061

PCT Pub. Date: Oct. 27, 2022

(65) Prior Publication Data

US 2024/0198062 A1 Jun. 20, 2024

Related U.S. Application Data

(60) Provisional application No. 63/177,547, filed on Apr. 21, 2021.

(51) Int. Cl.
*A61M 27/00* (2006.01)

(52) U.S. Cl.
CPC ... *A61M 27/002* (2013.01); *A61M 2205/3331* (2013.01); *A61M 2205/502* (2013.01)

(58) Field of Classification Search
CPC ........ A61M 27/002; A61M 2205/3334; A61M 1/3663; A61M 2025/024; A61M 39/288;
(Continued)

(56) References Cited

U.S. PATENT DOCUMENTS 8,740,865 B2 * 6/2014 Krystek .................. A61F 5/445 340/657
9,928,341 B2 * 3/2018 Angelides .............. G16H 40/67
(Continued)

*Primary Examiner* — Philip R Wiest
*Assistant Examiner* — Peter Daniel Smith
(74) *Attorney, Agent, or Firm* — Tarolli, Sundheim, Covell & Tummino LLP

(57) ABSTRACT

A medical drain device is provided. A drain inlet receives fluid flow from a patient. A drain outlet releases fluid flow to a reservoir. A sensor system is interposed fluidically between the drain inlet and the drain outlet. The sensor system produces a sensed flow pressure signal responsive to fluid travel between the drain inlet and the drain outlet. A flow regulator is interposed fluidically between the drain inlet and the drain outlet and is configured to selectively restrict at least a portion of fluid travel between the drain inlet and the drain outlet. A processor is configured to receive the sensed flow pressure signal and responsively produce at least one of a flow rate indication signal, a flow pressure indication signal, and a flow volume indication signal.

2 Claims, 7 Drawing Sheets

(58) Field of Classification Search
CPC ............ A61M 2027/004; A61M 1/734; A61M 1/743; G01F 1/37; G01F 1/372; G01F 1/383; G05D 7/0676; F16K 7/063; F16K 7/068; F16K 7/045
See application file for complete search history.

(56) References Cited

U.S. PATENT DOCUMENTS

| | | | | |
|---|---|---|---|---|
| 2018/0028794 | A1* | 2/2018 | Browd | A61B 5/031 |
| 2019/0358387 | A1* | 11/2019 | Elbadry | A61B 5/0059 |
| 2021/0262840 | A1* | 8/2021 | Boillat | G01F 1/36 |
| 2022/0062601 | A1* | 3/2022 | Morse | A61M 5/168 |

* cited by examiner

MEDICAL DRAIN DEVICE

RELATED APPLICATION

This application claims priority from U.S. Provisional Application No. 63/177,547, filed 21 Apr. 2021, the subject matter of which is incorporated herein by reference in its entirety for all purposes.

TECHNICAL FIELD

This disclosure relates to a medical drain device and a method for managing patient fluid drainage.

BACKGROUND

In certain situations, medical drains are used during and/or after a medical procedure to remove accumulated bodily fluids from a wound or surgical site. Managing fluid drain from a patient can present several challenges to the patient and the patient's caregivers. For example, some known drain management issues include, but are not limited to, insufficient monitoring of drainage volumes from post-operative patients, inaccurate or absent recordings on drainage volume due to personnel or technological limitations, and reliance on patients to manage their own drains outside of a medical care facility.

SUMMARY

In an aspect, alone or in combination with any other aspect, a medical drain device provided. The medical drain device includes a drain inlet for receiving fluid from a patient. A drain outlet releases fluid flow to a reservoir. A sensor system is interposed fluidically between the drain inlet and the drain outlet. The sensor system produces a sensed flow pressure signal responsive to fluid travel between the drain inlet and the drain outlet. A flow regulator is interposed fluidically between the drain inlet and the drain outlet and is configured to selectively restrict at least a portion of fluid travel between the drain inlet and the drain outlet. A controller is configured to receive the sensed flow pressure signal and responsively produce at least one of a flow rate indication signal, a flow pressure indication signal, and a flow volume indication signal.

In an aspect, alone or in combination with any other aspect, the sensor system includes a sensor housing having a housing input port in fluid communication with the drain inlet, a housing output port in fluid communication with the drain outlet, and a housing body interposed between the housing input and output ports. The housing input port, the housing output port, and the housing body define an inner housing chamber for fluid travel between the drain inlet and the drain outlet. At least one sensor is connected to the sensor housing and produces the sensed flow pressure signal responsive to fluid travel through the inner housing chamber.

In an aspect, alone or in combination with any other aspect, a method for managing patient fluid drain is provided. The method includes providing a medical drain device. The medical drain device includes a sensor system having first and second pressure sensors. A first flow pressure in the medical drain device is sensed with the first pressure sensor. A first flow pressure signal, which is responsive to the first flow pressure, is produced and transmitted with the first pressure sensor. A second flow pressure in the medical drain device is sensed with the second pressure sensor. A second flow pressure signal, which is responsive to the second flow pressure, is produced and transmitted with the second pressure sensor. The first and second sensed flow pressure signals are received at the processor. A differential pressure between the first and second flow pressures is determined from the received first and second sensed flow pressure signals with the processor. A flow rate, which is responsive to the determined differential pressure, is determined with the processor. A flow volume that has been drained from the patient is estimated as a function of the determined flow rate with the processor.

In an aspect, alone or in combination with any other aspect, the method for managing patient fluid drain can also include estimating a future flow volume accumulation as a function of the estimated flow volume and determined flow rate with the processor. The estimated future flow volume accumulation is compared with a predetermined future flow volume accumulation with the processor. At least a portion of fluid travel between the drain inlet and the drain outlet is restricted with the flow regulator if the estimated future flow volume accumulation is greater than the predetermined future flow volume accumulation.

In an aspect, alone or in combination with any other aspect, the method for managing patient fluid drain can also include producing a user-perceptible alert when the estimated future flow volume accumulation is greater than the predetermined future flow volume accumulation, and/or when the flow regulator restricts at least a portion of the fluid travel between the drain inlet and the drain outlet.

BRIEF DESCRIPTION OF THE DRAWINGS

For a better understanding, reference may be made to the accompanying drawings, in which.

DESCRIPTION OF EMBODIMENTS

Figure 1:
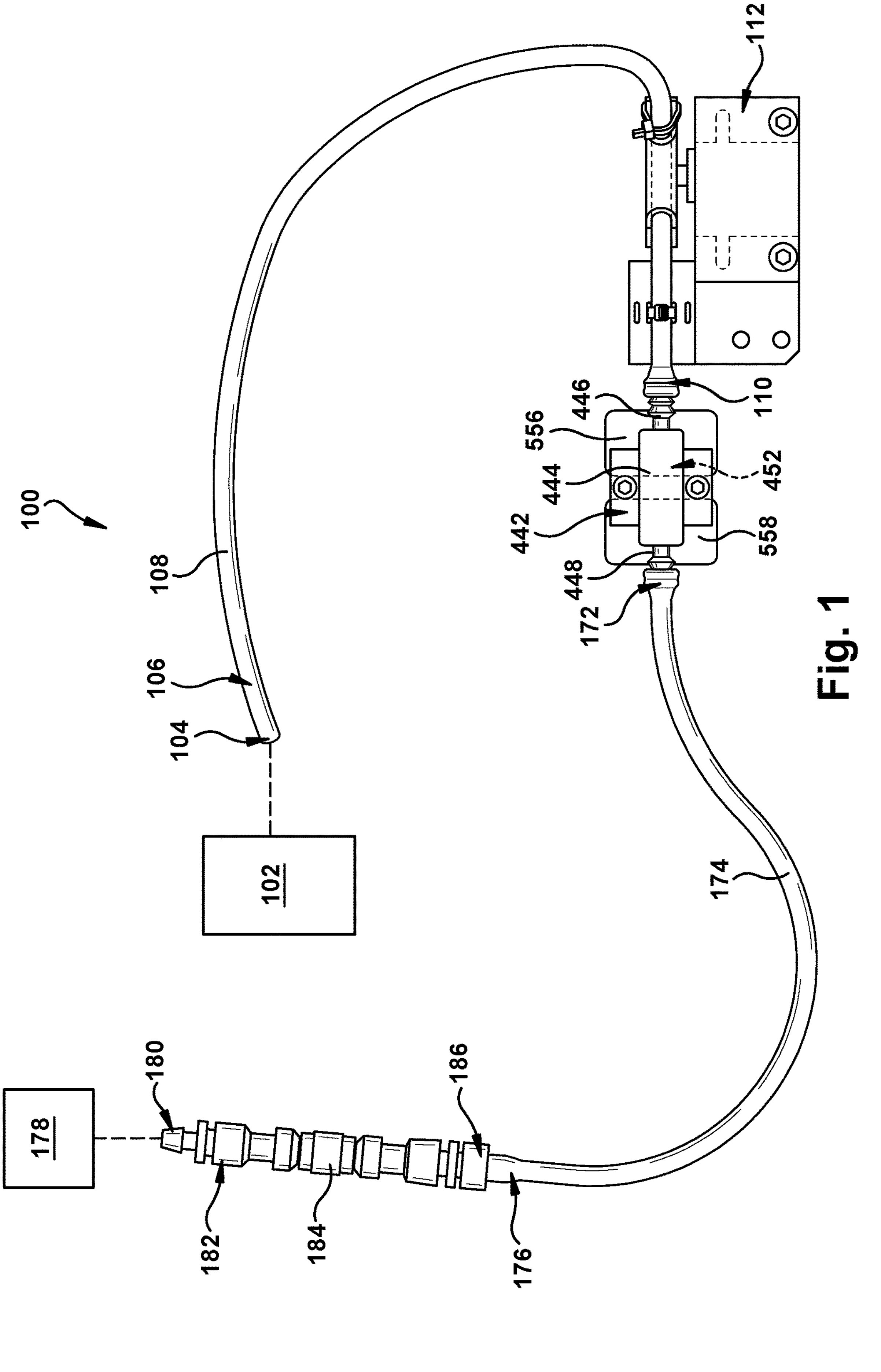
FIG. 1 schematically illustrates a medical drain device according to one aspect of the present invention, including the medical drain device in a first configuration.

Unless defined otherwise, all technical and scientific terms used herein have the same meaning as is commonly understood by one of ordinary skill in the art to which the present disclosure pertains.

As used herein, the term "patient" can refer to any warm-blooded organism including, but not limited to, human beings, pigs, rats, mice, birds, cats, dogs, goats, sheep, horses, monkeys, apes, rabbits, cattle, farm animals, livestock, etc.

As used herein, the term "caregiver" can be used interchangeably to refer to an individual who at least partially provides medical care to the patient in a medical care facility or in locations remote from a medical care facility.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" can be interpreted to include X and Y.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly connected" to another element, there are no intervening elements present. It will also be appreciated by those of skill in the art that references to a structure or feature that is disposed "adjacent" another feature may not have portions that overlap or underlie the adjacent feature.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or Figures unless specifically indicated otherwise.

The invention comprises, consists of, or consists essentially of the following features, in any combination.

FIG. 1 schematically illustrates a medical drain device 100 for managing fluids (bodily or otherwise) draining from a wound or surgical site of a patient 102. The draining fluids may include bodily fluids (e.g., pus, blood, and/or serous fluid), delivered fluids (e.g., water, IV fluids, and/or medicinal fluids), any other fluids that may accumulate at the wound or surgical site, or any combination thereof. The medical drain device 100 includes a drain inlet 104 for receiving fluid flow from the patient 102 in direct or indirect contact therewith. The drain inlet 104 may be inserted into a wound or surgical opening in the patient's body. Alternatively, the drain inlet 104 may be adjacent to or remote from the wound or surgical opening and in fluid communication with the wound or surgical opening via a separate intermediary medical instrument (not shown).

In the example configuration shown in FIG. 1, the drain inlet 104 is at a first inlet line end 106 of a fluid inlet line 108. The drain inlet 104 and at least a portion of the fluid inlet line 108 may be inserted directly into the wound or surgical opening to drain fluids from the wound or surgical site. At least a portion of the fluid inlet line 1008 may be inserted with the drain inlet 104 into the wound or surgical opening for draining fluids. Actively or passively provided negative pressure in the medical drain device 100 may responsively cause fluids at the wound or surgical site to be drawn through the drain inlet 104, into the fluid inlet line 108 and, thus, into the medical drain device 100.

Alternatively, the drain inlet 104 may be at a first end of a medical draining instrument configured to be positioned in the wound or surgical opening for draining fluids from the wound or surgical site, while the first inlet line end 106 is attached to a second end of the medical draining instrument to place the fluid inlet line 108 in fluid communication with the medical draining instrument. For example, the medical draining instrument may be an implantable drain (not shown), which can be selected from one or more known implantable drains configured to be positioned at least partially in the wound or surgical opening. The first inlet line end 106 may be selectively attached to a second end of the implantable drain to place the fluid inlet line 108 in fluid communication with the implantable drain. The implantable drain may include a suction member having one or more openings on an outside surface in fluid communication with an inside surface of the implantable drain. The suction member, for example, may be located near the drain inlet end of the implantable drain. Fluid from the surgical or wound site may be drawn into the drain inlet 104 of the implantable drain via the openings on the outside surface of the suction member and into the fluid inlet line 108 in fluid communication with the inside surface of the implantable drain.

The fluid inlet line 108 of FIG. 1 may be formed from an elastically deformable tube having the first inlet line end 106 and a second inlet line end 110, opposite the first inlet line end 106. Alternatively, the fluid inlet line 108 may be formed from a rigid tube or any other component capable of having fluids flow therethrough.

Figure 2:
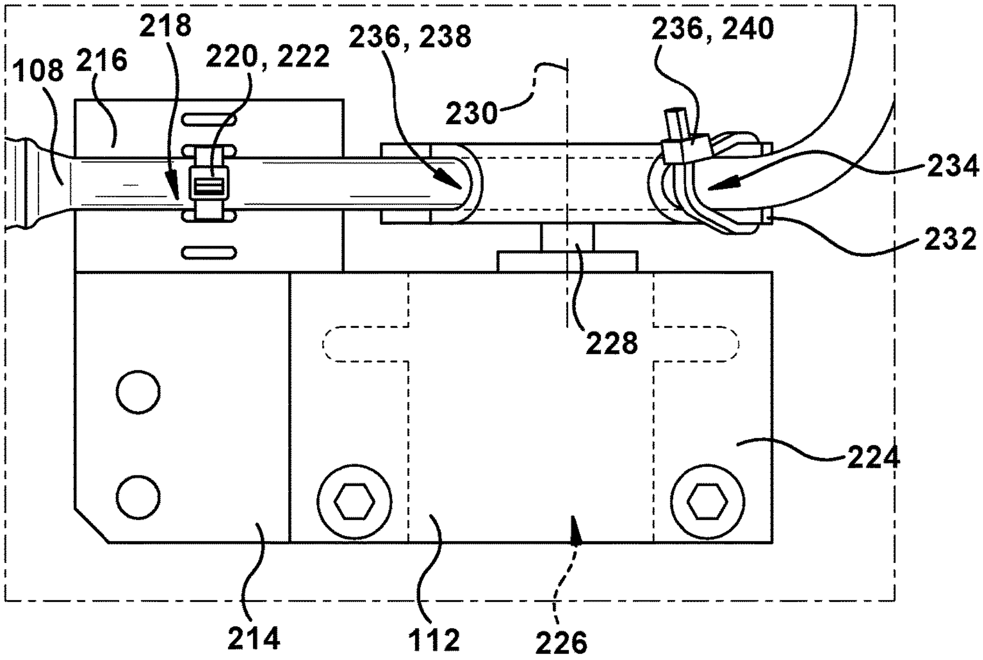
FIG. 2 is a top view of a component of the medical drain device of FIG. 1.
Figure 3:
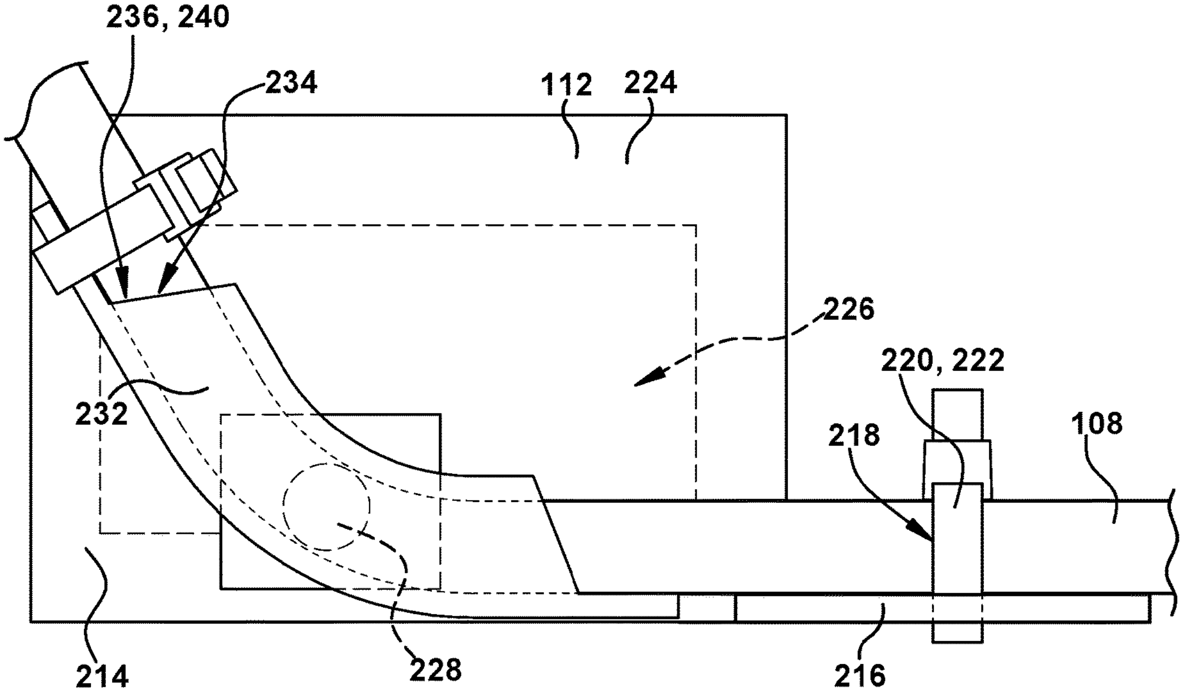
FIG. 3 is a side view of the component of FIG. 4.

The medical drain device 100 may include a flow regulator 112 selectively connected to the fluid inlet line 108 and interposed fluidically between the first and second inlet line ends 106, 110. The flow regulator 112 may be configured to selectively reversibly restrict at least a portion of fluid travel through the fluid inlet line 108 by selectively elastically deforming the fluid inlet line 108. For example, as shown in FIGS. 2-3, the flow regulator 112 may include a regulator housing 214 having an attachment portion 216 at which a stationary inlet line portion 218 of the fluid inlet line 108 may be selectively attached to the regulator housing 214. The stationary inlet line portion 218 may be attached to the attachment portion 216 via a first attachment mechanism 220. The first attachment mechanism 220 may be, or may include, a cable tie, a wire, a clip, an elastic clamp, an adhesive, a tube or channel sized for a press-fit or frictional engagement, a hook and loop fastener, a magnetic fastener, a snap fastener, a hook and eye fastener, a button, a zipper, a string and eye fastener, a saw tooth fastener, or any other attachment mechanism or combination of attachment mechanisms. In FIGS. 2-3, the first attachment mechanism 220 is a cable fastener 222 that is selectively wrapped and secured about both the stationary inlet line portion 218 and a portion of the attachment portion 216 to selectively hold the stationary inlet line portion 218 in a desired position on the attachment portion 216.

The regulator housing 214 also includes a motor portion 224 in which a motor 226 (e.g., a servo motor) is provided. The motor 226 includes an output shaft 228 that is rotatable about an axis of rotation 230 upon actuation of the motor 226. A regulator arm 232 may be attached to, or integrally formed with, the output shaft 228 in a rotationally fixed manner such that rotation of the output shaft 228 responsively causes the regulator arm 232 to rotate about the axis of rotation 230.

The regulator arm 232 may be selectively connected to a rotatable inlet line portion 234 of the fluid inlet line 108, which may be between the stationary inlet line portion 218 and the first inlet line end 106. The regulator arm 232 may be selectively connected to the rotatable inlet line portion 234 via a second attachment mechanism 236. The second attachment mechanism 236 may be, or may include, a cable tie, a wire, a clip, an elastic clamp, an adhesive, a tube or channel sized for a press-fit or frictional engagement, a hook and loop fastener, a magnetic fastener, a snap fastener, a hook and eye fastener, a button, a zipper, a string and eye fastener, a saw tooth fastener, or any other attachment mechanism or combination of attachment mechanisms. In the configuration shown in FIGS. 2-3, the second attachment mechanism 236 includes an inner arm channel 238 of the regulator arm 232. The inner arm channel 238 may be sized to form a press-fit or frictional engagement with the rotatable inlet line portion 234 such that the rotatable inlet line portion is selectively maintained in the inner arm channel 238 and substantially prevented from undesirably egressing from the inner arm channel 238. The second attachment mechanism 236, as shown in FIG. 2, may also include a cable fastener 240 that is selectively wrapped and secured about both the rotatable inlet line portion 234 and a portion of the regulator arm 232 to selectively hold the rotatable inlet line portion 234 in a desired positioned with respect to the regulator arm 232.

Although the regulator arm 232 and, correspondingly, the inner arm channel 238 are both shown as having a curved or arcuate configuration, the regulator arm 232 and/or the inner arm channel 238 may have a curvilinear configuration, substantially linear configuration, or any other desired configuration.

The attachment of the regulator arm 232 to the rotatable inlet line portion 234 may be such that the rotatable inlet line portion 234 is rotationally fixed to the regulator arm 232. Accordingly, selective rotation of the regulator arm 232 responsively causes the rotatable inlet line portion 234 to rotate about the axis of rotation 230. Because the stationary inlet portion 218 is held stationary, selective rotation of the rotatable inlet line portion 234 in a first direction at least partially elastically bends the fluid inlet line 108 between the stationary and rotatable inlet line portions 218, 234. Bending the fluid inlet line 108 elastically deforms the fluid inlet line 108 and thereby restricts at least a portion of fluid travel through the fluid inlet line 108. A flow rate of fluids through the fluid inlet line 108 (and, thus, the medical drain device 100 as a whole) may decrease as the level of fluid travel restriction increases. After the fluid inlet line 108 is bent, selective rotation of the rotatable inlet line portion 234 in a second direction, opposite the first direction, may at least partially unbend the fluid inlet line 108 to reduce the amount of elastic deformation in the fluid inlet line 108 and lessen the level of fluid travel restriction. Therefore, the flow rate of fluids through the fluid inlet line 108 (and, thus, the medical drain device 100 as a whole) may be increased by decreasing the level of fluid travel restriction in the fluid inlet line 108.

The degree at which the fluid inlet line 108 is elastically bent/deformed, and thus, the level of fluid travel restriction, may directly correspond to the degree at which the regulator arm 232 is rotated by the motor 226 about the axis of rotation 230. In other words, the regulator arm 232 (and, accordingly, the rotatable inlet line portion 234) may be rotated by the motor 226 to various rotational positions, wherein each rotational position directly corresponds to a particular amount of reversible bending/deformation in the fluid inlet line 108 and to a particular level of fluid travel restriction in the fluid inlet line 108. Therefore, by controlling the rotational position of the regulator arm 232 with the motor 226, the level of fluid travel restriction in the fluid inlet line 108 and the flow rate of fluids through the medical drain device 100 can be controlled as desired.

The flow regulator 112 may have pre-set fluid travel-restriction states (which can alternatively be referred to as, for example, fluid inlet line-deformation states, fluid inlet line-bending states, and/or regulator arm rotation states) that directly correspond to varying flow states for fluids draining from the patient 102 through the medical drain device 100. For example, in certain use environments, the flow regulator 112 may be configured to produce three different fluid travel-restriction states (0%, 50%, and 100% restriction) that correspond to three different flow states (100%, 50%, and 0% flow) for fluids exiting the patient 102. In the 100% fluid travel-restriction and 0% flow state, the motor 226 is actuated to rotate the regulator arm 232 into a position in which a kink is formed in the fluid inlet line 108 to substantially prevent fluid from traveling through the fluid inlet line 108.

Although the rotatable inlet line portion 234 of the fluid inlet line 108 has been described as being rotated by the motor 226 via the output shaft 228 and the regulator arm 232, it is contemplated that the rotatable inlet line portion 234 may be operably connected to an output of the motor 226 in any desired manner as long as the motor 226 can be selectively controlled to rotate the rotatable inlet line portion 234 about the axis of rotation 230 as desired.

Furthermore, instead of, or in addition to, the elastic deformation of the fluid inlet line 108 being caused by bending the fluid inlet line 108, the flow regulator 112 (e.g., the regulator arm 232) may be configured to deform the fluid inlet line 108 and at least partially restrict fluid travel in any other manner, such as by, for example, by pinching, clamping, or cinching the fluid inlet line 108. Alternatively, the flow regulator 112 may be configured to at least partially restrict fluid travel through the fluid inlet line 108 without deforming the fluid inlet line 108. In such a configuration, the flow regulator 112 may comprise, for example, a pressure regulator valve, a "Luer-lock" style valve, a stopcock, any other type of valve, any other mechanism having one or more components that are selectively movable in order to at least partially restrict fluid travel through the fluid inlet line 108, or any combination thereof.

Figure 4:
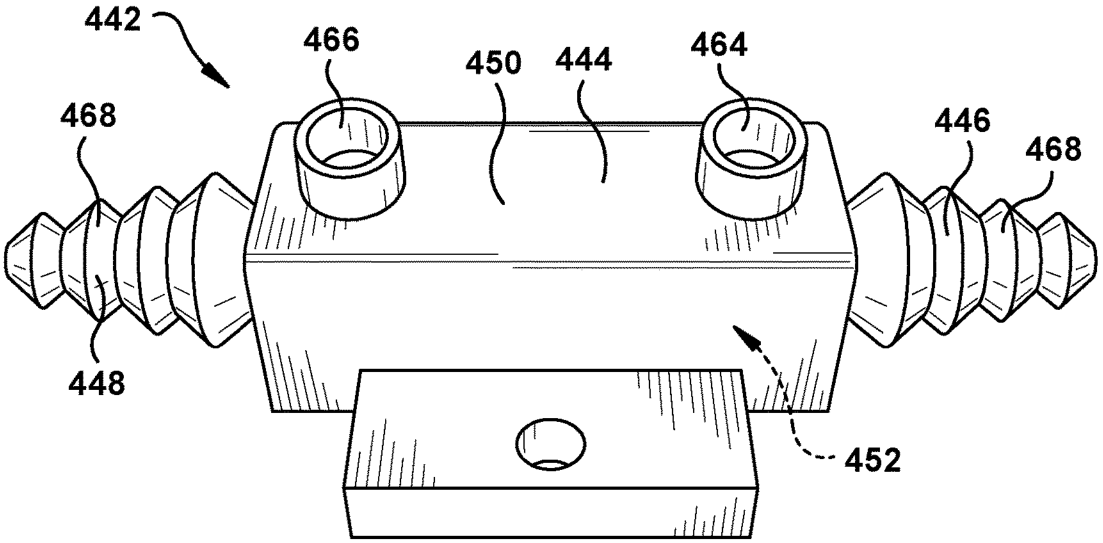
FIG. 4 is a perspective bottom view of a portion of another component of the medical drain device of FIG. 1.
Figure 5:
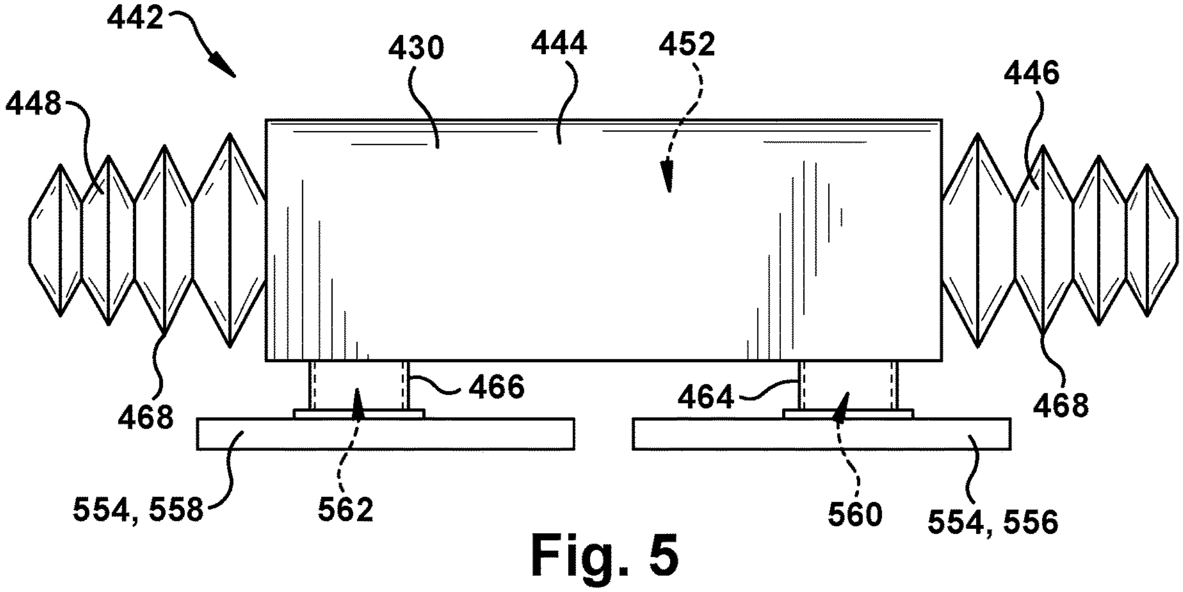
FIG. 5 is a side view of another portion of the component of FIG. 4.

As shown in FIGS. 1 and 4-5, the medical drain device 100 includes a sensor system 442 selectively connected to the second inlet line end 110 and in fluid communication with the fluid inlet line 108. As shown in FIGS. 4-5, the sensor system 442 may include a sensor housing 444. The sensor housing 444 includes a housing input port 446, a housing output port 448, and a housing body 450 interposed between the housing input and output ports 446, 448. The housing input port 446, the housing output port 448, and the housing body 450 collectively define an inner housing chamber 452 for fluid travel through the sensor system 442. Although the sensor housing 444 is shown as having only one housing input port 446 and one housing output port 448, the sensor housing can have any number of housing input and output ports 446, 448.

The sensor system 442 also includes at least one sensor 554 selectively connected (removably or permanently) to the sensor housing 444 for sensing fluid characteristics of fluid flowing through the inner housing chamber 452. For example, the at least one sensor 554 may be one or more of a pressure sensor for sensing fluid pressure in the inner housing chamber 452, a differential pressure sensor for sensing a difference in fluid pressure between two points in the inner housing chamber 452, a flow meter (e.g., an impeller flow meter, an ultrasonic sound-based flow meter, an optical absorbance-based flow meter, a strain gauge, and/or a magnetic-based flow meter) for measuring a flow rate of fluids through the inner housing chamber 452, any other sensor configured to sense fluid characteristics, or any combination thereof.

In the example configuration shown in FIG. 4, the at least one sensor 554 may be of a differential pressure type sensor, which includes at least first and second pressure sensors 556, 558. The first and second pressure sensors 556, 558 include first and second sensor ports 560, 562, respectively, for selectively operably connecting the first and second pressure sensors 556, 558 to the sensor housing 444. Each of the first and second pressure sensors 556, 558 may include sensing circuitry (not shown) in fluid communication with an associated one of the first and second sensor ports 560, 562.

As shown in FIGS. 4-5, the sensor housing 444 has a first connector port 464 adjacent the housing input port 446, and a second connector port 466 adjacent the housing output port 448. The first connector port 464 is configured to be selectively connected to (e.g., by selectively receiving) the first sensor port 560. When connected to the first connector port 464, the first sensor port 560 (and, accordingly, the sensing circuitry of the first pressure sensor 556) is in fluid communication with the inner housing chamber 452. An O-ring or other sealing member (not shown) may be inserted between the attached first connector port 464 and first sensor port 560 to help provide a substantially fluid-tight seal between the attached first connector port 464 and first sensor port 560. Similarly, the second connector port 466 is configured to be selectively connected to (e.g., by selectively receiving) the second sensor port 562. The second sensor port 562 (and, accordingly, the sensing circuitry of the second pressure sensor 558) is in fluid communication with the inner housing chamber 452 when connected to the second connector port 466. An O-ring or other sealing member (not shown) may also be inserted between the attached second connector port 466 and second sensor port 562.

Although the sensor housing 444 is shown as having two connector ports 464, 466, the sensor housing 444 may have any desired number of connector ports. The number of connector ports for a particular sensor housing 444 may be chosen, for example, based upon the number of sensors 554 attached to the sensor housing 444 and/or the manner in which each sensor 554 is configured to be connected to the sensor housing 444.

For reasons that will be discussed in more detail below, the first pressure sensor 556 is configured to sense a first flow pressure in the inner housing chamber 452 adjacent the first connector port 464 and responsively produce a first sensed flow pressure signal. Similarly, the second pressure sensor 558 is configured to sense a second flow pressure in the inner housing chamber 452 adjacent the second connector port 466 and responsively produce a second sensed flow pressure signal.

As shown in FIGS. 4-5, the housing input port 446 may include one or more barbs 468 (here, a plurality of barbs 468) or other interference-fit features for removably securing the second inlet line end 110 to the sensor housing 444. The second inlet line end 110 may be fit over at least one of the barbs 468 of the housing input port 446 when selectively connected to the housing input port 446. The barbs 468 may sequentially decrease in diameter as the housing input port 446 extends away from the housing body 450. This particular barb configuration allows the housing input port 446 to fit multiple diameters of fluid inlet lines 108.

As shown in FIG. 1, when the second inlet line end 110 is selectively connected to the housing input port 446, the inner housing chamber 452, the fluid inlet line 108, and the drain inlet 104 are in fluid communication with one another. Because of this fluid communication, fluid at the wound or surgical site drains from the wound or surgical site into the medical drain device 100 through the drain inlet 104, flows into the inner housing chamber 452 via the fluid inlet line 109, and flows through the inner housing chamber 452 where the first and second pressure sensors 556, 558 sense the first and second flow pressures in the fluid flow.

As shown in FIGS. 4-5, the housing output port 448 also includes one or more barbs 468 (here, a plurality of barbs 468) or other interference-fit features. The barbs 468 of the housing output port 448 are for removably securing a first outlet line end 172 of a fluid outlet line 174 to the sensor housing 444. The first outlet line end 172 may be fit over at least one of the barbs 468 of the housing output port 448 when selectively connected to the housing output port 448. As shown in FIGS. 4-5, the barbs 468 of the housing output port 448 may be shaped similarly to that of the barbs 468 of the housing input port 446.

The fluid outlet line 174 of FIG. 1 may be formed from an elastically deformable tube having the first outlet line end 172 and a second outlet line end 176, opposite the first outlet line end 172. Alternatively, the fluid output line 174 may be formed from a rigid tube or any other component capable of having fluids flow therethrough. The second outlet line end 176, as shown in FIG. 1, may be selectively connected to and placed in fluid communication with a reservoir 178 via a drain outlet 180.

The drain outlet 180 is configured to release fluid flow in the medical drain device 100 to the reservoir 178. The drain outlet 180 may be selectively inserted into the reservoir 178. Alternatively, the drain outlet 180 may be adjacent to or remote from the reservoir 178 and in fluid communication with the reservoir 178 via a separate intermediary medical instrument (not shown).

In FIG. 1, the drain outlet 180 is at a first connector end 182 of a reservoir connector 184. The first connector end 182 is configured to be releasably connected to the reservoir 178. A second connector end 186 of the reservoir connector 184 is selectively attached to the second outlet line end 176 such that the fluid outlet line 174 is in fluid communication with reservoir connector 184. Instead of being selectively attached to one another, the fluid outlet line 174 and the reservoir connector 184 may be integrally formed as a single unitary or monolithic piece.

The reservoir connector 184 is configured to securely join the fluid outlet line 174 to the reservoir 178 such that fluids traveling through the fluid outlet line 174 are released into the reservoir 178 when the reservoir connector 184 is connected to the reservoir 178. The secure connection may be the result of the reservoir connector 184 having a multi-step connection/disconnection process for joining and removing the reservoir connector 184 to and from the reservoir 178. This multi-step process reduces the risk of spillage, unintentional connection, and/or unintentional disconnection because multiple intentional steps are required to connect and disconnect the reservoir connector 184 to and from the reservoir 178, when this type of reservoir connector 184 is present. The multi-step process may involve, for example, inserting and twisting motions, as with a bayonet-type connection. Furthermore, the drain outlet 180 at the first connector end 182 of the reservoir connector 184 may be configured such that the drain outlet 180 is closed (i.e., sealed) until the first connector end 182 is securely connected to the reservoir 178, in order to reduce the risk of spillage.

Alternatively, the drain outlet 180 may be at the second outlet line end 176 of the fluid outlet line 174. In such case, the drain outlet 180 may be inserted directly into the reservoir 178 or directly connected to a portion of the reservoir 178.

The reservoir 178 may be any container configured to accumulate fluids drained from the surgical or wound site. In addition to holding drained fluids, the reservoir 178 may double as a passive source of negative pressure for drawing fluids from the wound or surgical site into the medical drain device 100. In such case, the reservoir 178 may be, for example, a negative pressure bulb (e.g., a bulb of a Jackson-Pratt drain), an expandable container (e.g., a fluid container of a Hemovac drain), a sealed enclosure (e.g., a vacuum bottle of a PleurX drain), any other reservoir capable of being used to hold fluids and/or generate negative pressure in the medical drain device 100, or any combination thereof. Alternatively, the reservoir 178 may be fluidically interposed between the surgical or wound site and an active source of negative pressure (e.g., a vacuum or suction line).

As shown in FIG. 1, when the fluid outlet line 174 is selectively connected to the housing output port 448 via the first outlet line end 172 and the reservoir 178 via the reservoir connector 184, the inner housing chamber 452, the fluid outlet line 174, the drain outlet 180, the reservoir connector 184, and the reservoir 178 are in fluid communication with one another. Because of this fluid communication, fluid drains from the inner housing chamber 452 of the sensor system 442 into the fluid outlet line 174, and flows into the reservoir 178 via the fluid outlet line 174 and the reservoir connector 184. The sensor system 442 thus is interposed fluidically between the drain inlet 104 and the drain outlet 180 so that substantially all fluids entering the medical drain device 100 through the drain inlet 104 travel through the sensor system 442 before being released into the reservoir 178 via the drain outlet 180.

Figure 6:
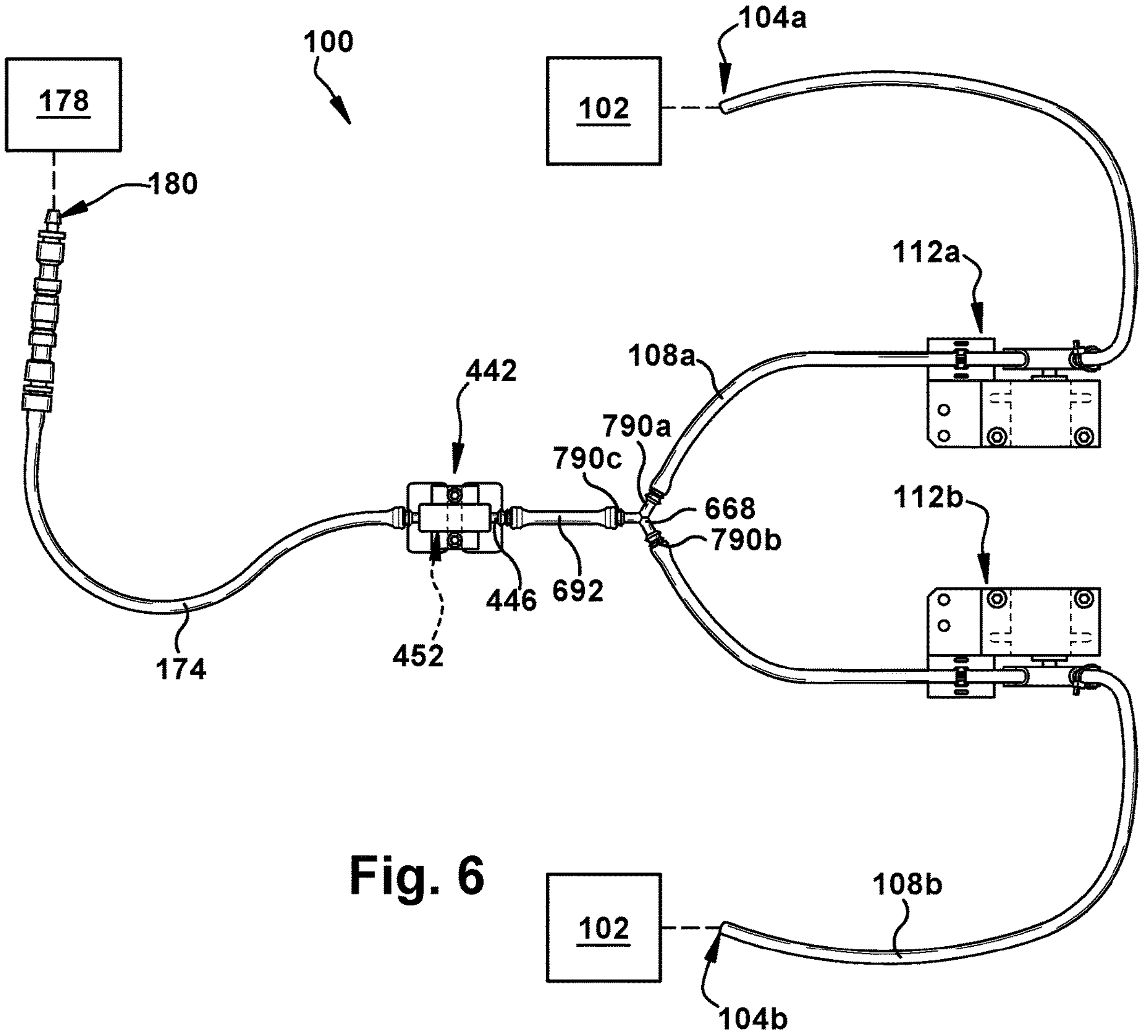
FIG. 6 schematically illustrates the medical drain device of FIG. 1 in a second configuration.

Although the medical drain device 100 is shown in FIG. 1 as having only one fluid inlet 104, the medical drain device 100 may be configured to have a plurality of fluid inlets 104. For example, the medical drain device is shown in FIG. 6 as having a plurality of fluid inlets 104 (shown here as 104*a* and 104*b*), a plurality of fluid inlet lines 108 (shown here as 108*a* and 108*b*), and a plurality of flow regulators 112 (shown here as 112*a* and 112*b*). Each flow regulator 112*a*, 122*b* is interposed fluidically between the drain outlet 180 and an associated one of the drain inlets 104*a*, 104*b*, and is configured to restrict at least a portion of fluid travel being the associated drain inlet 104*a*, 104*b* and the drain outlet 180. The medical drain device 100 of FIG. 6, however, includes only one sensing system 442 for sensing the fluid characteristics of fluid flowing through the sensing system 442 from each of the fluid inlets 104. Therefore, in order to merge fluids entering the medical drain device 100 from each of the drain inlets 104*a*, 104*b* into a single flow for traveling through the single sensing system 442, the medical drain device 100 may include a splitter 688 interposed fluidically between the sensor system 442 and the plurality of drain inlets 104*a*, 104*b*.

Figure 7:
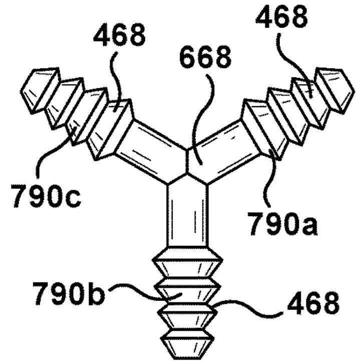
FIG. 7 is a top view of a component of the medical drain device of FIG. 6.

FIG. 7 depicts an example splitter 688 that may be utilized in a multi-drain inlet medical drain device 100. The splitter 688 includes multiple splitter ports 790 (shown here as 790*a*, 790*b*, 790*c*). Each of the splitter ports 790*a*, 790*b*, 790*c* may include one or more barbs 468 or other interference-fit features. The barbs 468 of each splitter port 790*a*, 790*b*, 790*c* may be shaped similarly to that of the barbs 468 of the housing input and output ports 446, 448.

In the example configuration shown in FIG. 6, a first one of the splitter ports 790*a* is selectively connected to and in fluid communication with a first one of the drain inlets 104*a* via a first one of the fluid inlet lines 108*a*, and a second one of the splitter ports 790*b* is selectively connected to and in fluid communication with a second one of the drain inlets 104*b* via a second one of the fluid inlet lines 108*b*. A third one of the splitter ports 790*c* is in fluid communication with the housing input port 446 (and, thus, the inner housing chamber 452) via a connecting line 692. The connecting line 692, similarly to that of the fluid inlet line 108, may be an elastically deformable tube, a ridged tube, or any other component capable of having fluids flow therethrough. The splitter 688 thus merges merge fluids entering the medical drain device 100 from each of the drain inlets 104*a*, 104*b* into a single flow that exits the splitter 688 and flows into the sensing system 442 via the connecting line 692.

Figure 8:
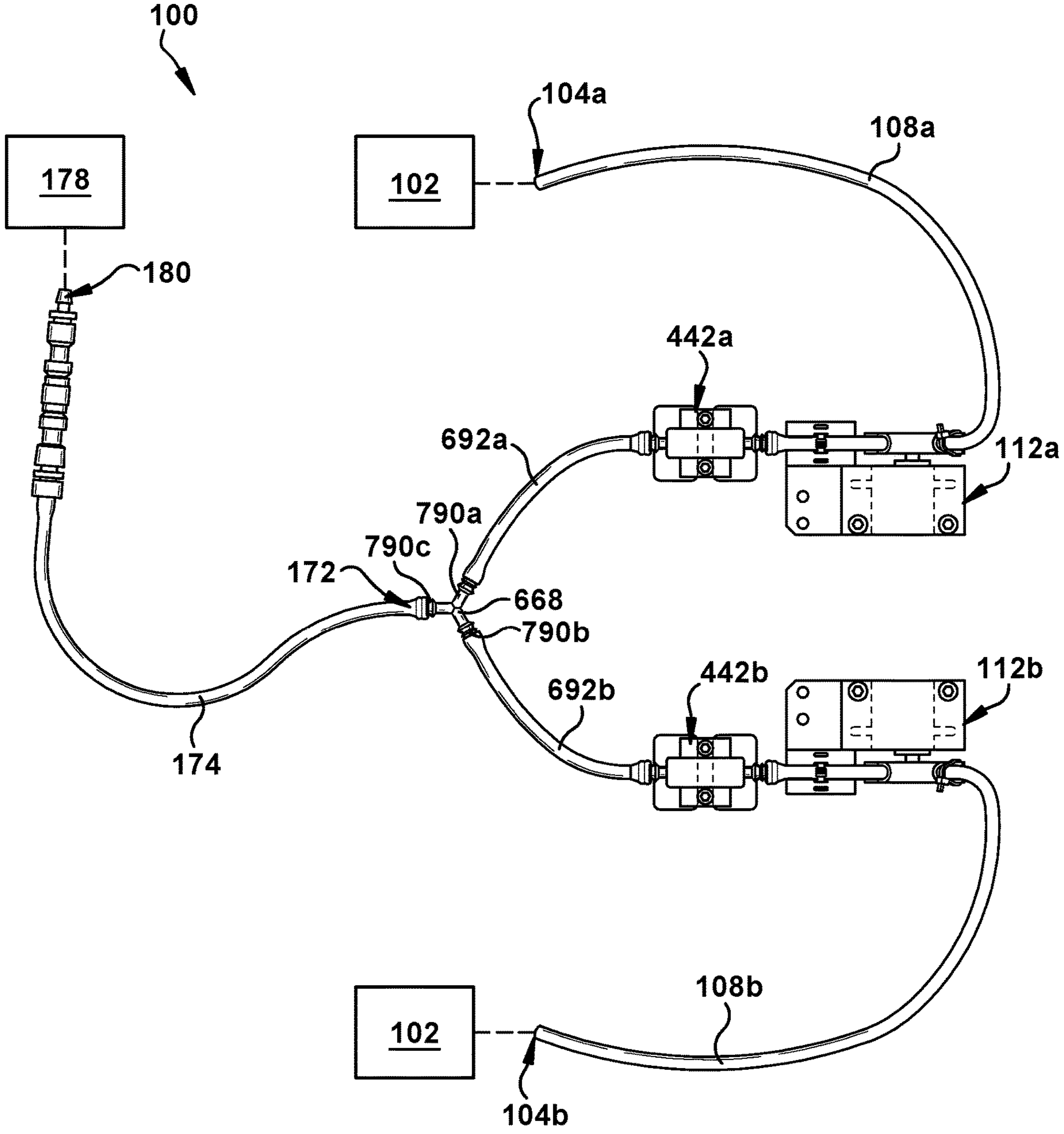
FIG. 8 schematically illustrates the medical drain device of FIG. 1 in a third configuration.

The medical drain device 100 shown in FIG. 8, in contrast to that of FIG. 7, includes a plurality of sensing systems 442 (shown in FIGS. 8 as 442*a* and 442*b*). Each sensor system 442*a*, 442*b* of the medical drain device 100 of FIG. 8 is interposed fluidically between the drain outlet 180 and an associated one of the drain inlets 104*a*, 104*b* and produces at least one flow pressure signal responsive to fluid travel between an associated drain inlet 104*a*, 104*b* and the drain outlet 180. The medical drain device 100 of FIG. 8, however, includes only one fluid outlet line 174 for directing fluids to the drain outlet 180 and the reservoir 178. Therefore, in order to merge fluids exiting from each of the sensing systems 442*a*, 442*b* into a single flow for traveling through the single fluid outlet line 174 to the drain outlet 180, the medical drain device 100 may include the splitter 688 interposed fluidically between the multiple sensor systems 442*a*, 442*b* and the drain outlet 180.

In the example configuration shown in FIG. 8, a first one of the splitter ports 790*a* is selectively in fluid communication with a first one of the sensing systems 442*a* via a first connecting line 692*a*, and a second one of the splitter ports 790*b* is selectively in fluid communication with a second one of the sensing systems 442*b* via a second connecting line 692*b*. The first and second connecting lines 692*a*, 692*b* may be constructed similarly to the connecting line 692 of FIG. 6. The first outlet line end 172 is connected to a third one of the splitter ports 790*c* such that the splitter 688 is in fluid communication with the drain outlet 180 via the fluid outlet line 174. Therefore, fluids exiting each of the sensing systems 442*a*, 442*b* are directed into the splitter 688 via the first and second connecting lines 692*a*, 692*b*. The splitter 688 then merges these fluids into a single flow that exits the splitter 688 and flows into the fluid outline line 174 toward the drain outlet 180.

Accordingly, through the use of a splitter 688, the medical drain device 100 can be modified to have multiple fluid inlets 104 (along with multiple other components). Having multiple fluid inlets 104 may be desirable when there are multiple wound or surgical sites on a single patient 102 that would benefit from fluid drain. Multiple fluid inlets 104 may also be beneficial at a single wound or surgical site having a heavy flow of fluid draining from the wound or surgical site.

Figure 9:
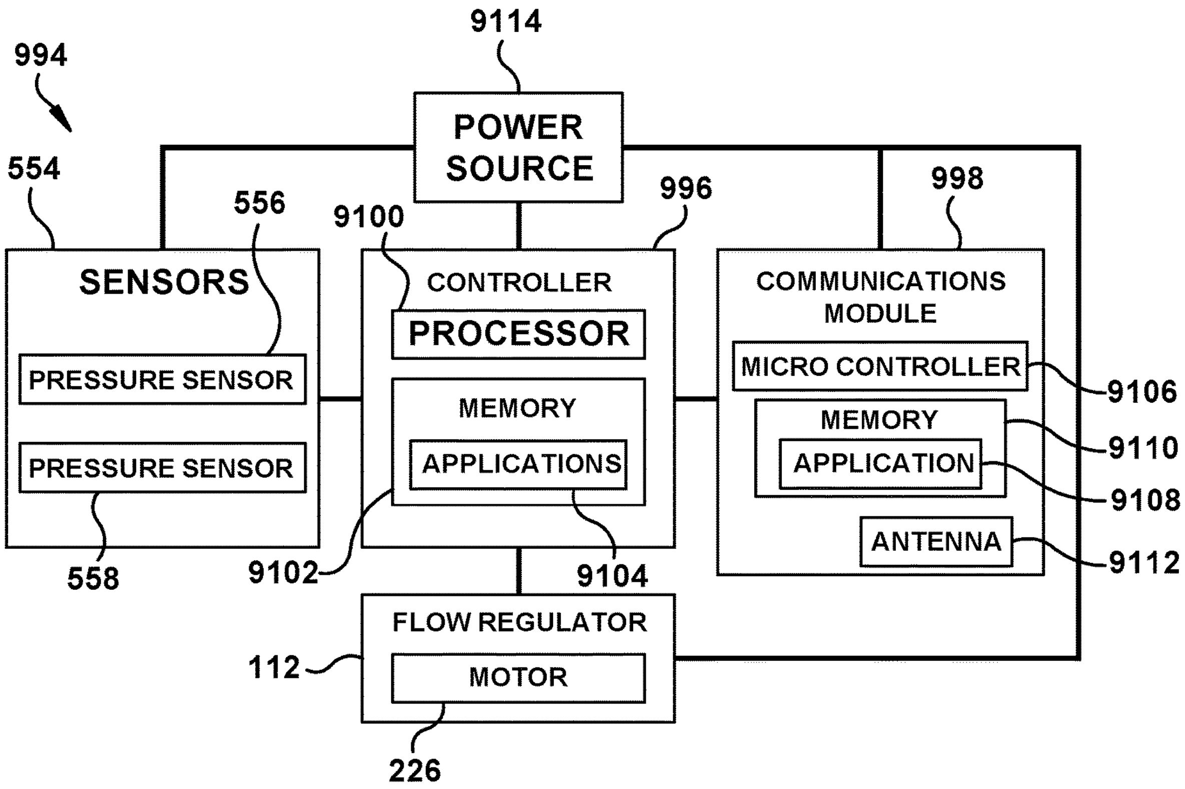
FIG. 9 schematically illustrates an example system of the medical drain device of FIG. 1.

FIG. 9 illustrates an example an electronic drain management system 994 of the medical drain device 100 depicted in FIG. 1. The drain management system 994 includes the one or more sensors 554 coupled to a controller 996. The controller 996, in one example, is operably coupled to a communications module 998 to send, and in some examples receive, communications. Additionally, the controller 994 can be configured to selectively operate the flow regulator 112.

In the example configuration, the one or more sensors 554 include the first and second pressure sensors 556, 558. Each of the first and second pressure sensors 556, 558 are configured to sense flow pressure in the inner housing chamber 452, responsively produce a sensed flow pressure signal, and output the sensed flow pressure signal.

The controller 996 may include circuitry to receive sensed flow pressure signals directly or indirectly from the first and second pressure sensors 556, 558, process raw data from the sensed flow pressure signals into relevant parameters, provide output signals to the communications module 998 and flow regulator 112, and receive and process signals from communications module 998. In one example, the controller 996 may include a processor 9100 and a memory 9102. The processor 9100 may include a microcontroller for one or more embedded applications 9104 in the memory 9102, such as a small computing device on a single integrated circuit including one or more processor cores, memory, and programmable input/output peripherals. The memory 9102 may include nonvolatile or programmable memory, such as flash memory and one-time programmable read only memory (ROM), which may include, for example, computer implemented instructions for controlling the processor 9100. The memory 9102 may also include volatile memory, such as random access memory (RAM), for holding computer implemented instructions and computer readable data for controlling the processor 9100.

The processing of signals may be implemented in a combination of hardware and computer programming in the controller 996. For example, the computer programming may be processor-executable instructions stored on at least one non-transitory machine-readable storage medium, such the memory 9102. The hardware may include at least one processor 9100 to execute the processor-executable instructions. In some examples, the hardware may also include other electronic circuitry to at least partially implement at least one feature of the processing. The information generated from the processing may be stored as data in the memory 9102. This data may include information responsive to the sensed flow pressure signals, as well as other information regarding the patient 102, coefficients, times, and/or the medical drain device 100 that may be used to process the sensed flow pressure signals or signals from the communications module 998.

As will be discussed in more detail below, based on the sensed flow pressure signals received from the first and second pressure sensors 556, 558, the controller 996 may determine relevant parameters such as, but not limited to, a flow pressure, a flow rate, a flow volume (estimated or actual) of drained fluid, as well as estimate a future flow volume accumulation.

If, for example, the controller 996 determines that the estimated future flow volume accumulation is greater than a stored predetermined future flow volume accumulation, the controller 996 may automatically provide a signal to the flow regulator 112 to operate the motor 226 to rotate the regulator arm 232 to at least partially restrict the fluid travel through the medical drain device 100. Alternatively, or additionally, the controller 996 may provide a notification to the patient 102, a caregiver, and/or a remote care center to warn of potential of unexpectedly large drainage amounts (i.e., the estimated future flow volume accumulation being greater than the stored predetermined future flow volume accumulation). The controller 996 may also be instructed by the patient 102, the caregiver, and/or the remote care center to control the flow regulator 112 to increase or decrease the level of fluid travel restriction as desired. Therefore, the amount to which the flow regulator 112 deforms the fluid inlet line 108 and restricts fluid travel through the fluid inlet line 108 may be set at least partially in response to at least one of a user command and one or more variables that are responsive to the sensed flow pressure signals.

The communications module 998 can be configured to include a wireless-network connectivity microcontroller 9106 for an embedded application 9108 stored in a memory 9110, such as a small computing device on a single integrated circuit including a processor core, memory, and programmable input/output peripherals.

The memory 9110 may include, for example, computer implemented instructions for controlling the communications module 998. Optional features of the communications module 998 may include input/output serial ports, such as universal asynchronous receiver/transmitter (UART) or other serial communication interfaces such as inter-integrated circuits (I2C). The communications module 998 may include one or more network processors subsystems for network-on-a-chip having a dedicated processor and memory for radio, baseband, and media access control (MAC) with encryption features as well as embedded internet protocol suite (TCP/IP) and cryptographic protocols (TLS/SSL) stacks, hypertext transfer protocol (HTTP) server, and other network protocols.

Additionally, the communications module 998 may include a wireless-network antenna 9112. The antenna 9112 may be low profile and configured to conserve space. The antenna 9112 may be, for example, a printed inverted F antenna, a patch antenna, a ceramic antenna, or any other type of antenna.

Signals representative of sensor measurements or processed parameters responsive to sensor measurements may be stored as data with other patient or relevant information within the memory 9110. In one example, the data, particularly data that is transmitted via communications module 998, may be encrypted to protect patient health information. The encrypted data may be deleted after it is transferred from the medical drain device 100.

In one aspect, determining a flow volume could be used to determine if the fluid is nearing, or has reached, a predetermined volume amount, such as a maximum volume and/or a warning-level volume, of the reservoir 178. If so, the controller 996 could provide a message via the communications module 998, via an indicator light or sound, written message, and/or other notification, to the patient 102 or the caregiver to alert the patient 102 or the caregiver that the reservoir 178 is full. Similarly, a notification may be provided if the estimated future flow volume accumulation is greater than the stored predetermined future flow volume accumulation, and/or if the flow rate is determined to be outside of stored flow rate parameters over a period of time. In some examples, the stored parameters (e.g., the selected volume amount, the stored predetermined future flow volume accumulation value, and/or the stored flow rate parameters) may be stored in the memory 9102 and compared with the determined/estimated values via the processor 9100 of the electronic drain management system 994. In other examples, the sensed flow pressure signals may be transmitted to a remote computing device that processes the signals, determines the relevant parameters from the flow pressure signals, compares the relevant parameters to stored parameters as necessary, and outputs relevant information for alerting the patient or the caregiver or for the patient 102 or the caregiver to review.

The electronic drain management system 994 may also include a power source 9114, such as a rechargeable battery or a single-use battery, in electrical communication with at least one of the sensors 554, the controller 996 (e.g., the processor 9100 and/or the memory 9102), the communications module 998, the flow regulator 112, and any other electronic component to selectively provide electrical power to the electrically connected components. The controller 996 may be configured to determine a power level of the power source 9114 and notify the patient 102 or the caregiver if the power level of the power source 9114 falls below a stored power level value. A corded mains power supply (not shown) could also or instead be provided to the electronic drain management system 994.

Figure 10:
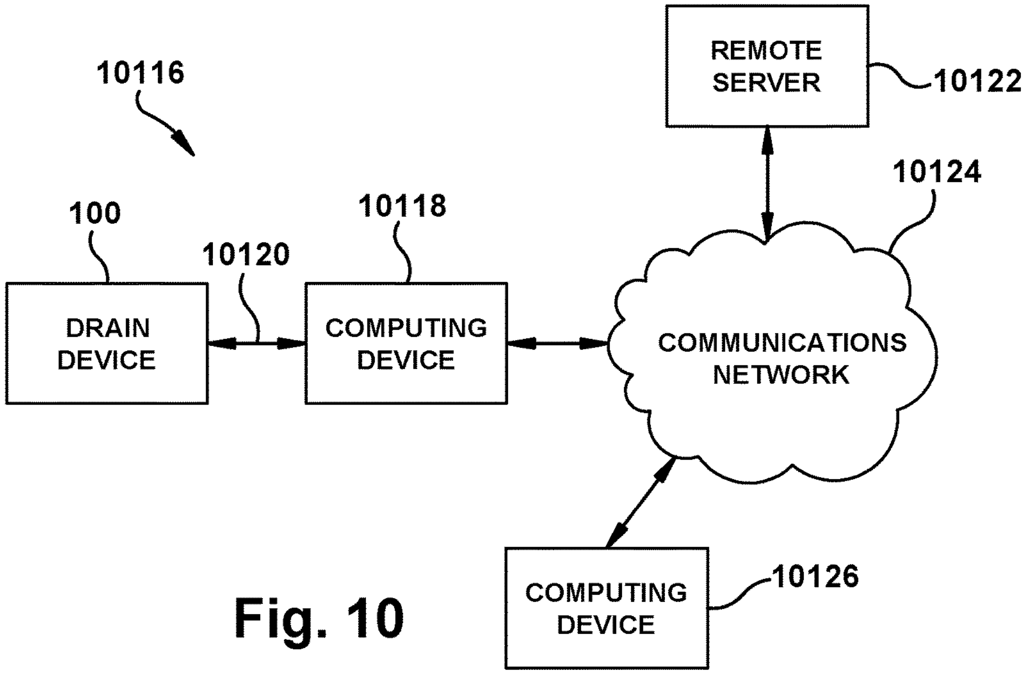
FIG. 10 schematically illustrates an example system that includes the medical drain device of FIG. 1.

FIG. 10 illustrates an example communications system 10116 for use with medical drain device 100. The communications module 998 of the medical drain device 100 may communicate directly with a computing device 10118 over a wireless-network 10120. The computing device 10118 may be configured to exchange data from the medical drain device 100, or data processed from data received from the medical drain device 100 with a remote server 10122 via a communications network 10124, e.g., a local area network or wide area network such as the Internet or other network. The remote server 10122 may include or have access to the patient's electronic medical record so that data transferred to the remote server 10122 may be uploaded to the patient's electronic medical record. In one example, a second computing device 10126 may access the data related to the medical drain device 100 on the remote server 10122 via an application over the communications network 10124.

The communications module 998 may exchange data with the computing device 10118, which may include a mobile device, a wearable device, a laptop, and/or a network intermediary, via a wired connection and/or a wireless technology. The computing device 10118 may then exchange the received data or additional processed data, over the communications network 10124 with the remote server 10122, which, in one example, is located in a data center. The patient 102 or the caregiver may access the remote server 10122 via the second computing device 10126, which may include a laptop, a desktop, a workstation, a mobile device, or in some examples, via the computing device 10118.

The computing device 10118 may include a general purpose mobile device such as a smartphone or tablet, a laptop or other computing device, a wearable device, or a special purpose medical device configured to exchange data with the medical drain device 100. The computing device 10118 may be provided with a computer program configured to relay data from the medical drain device 100 to the remote server 10122, such as information processed by the controller 996, and, in some examples, receive information from the remote server 10122 and provide the received information to the communications module 998, such as firmware updates or executable instructions. Additionally, the computer program of the computing device 10118 may be configured to present data from the communications module 998 in a form that is usable by the patient 102 or the caregiver, such as through a user interface that can clearly display relevant patient or drain management information, alert the patient 102 or the caregiver that the fluid regulator 112 is restricting fluid travel between the drain inlet 104 and the drain outlet 180, and/or alert the patient 102 or the caregiver to increase or decrease the level of fluid travel restriction. Also, the user interface may allow the patient 102 or the caregiver to interact with the medical drain device 100, such as by providing controls that may control the flow regulator 112, disable an alarm, reprogram a flow rate variable, and/or any other desired interaction. Still further, the user interface may be configured to present information from the remote server 10122 to the patient 102 or the caregiver.

The communications module 998 may be configured to exchange data in the wireless-network 10120 with the computing device 10118 in a variety of manners. For example, the communications module 998 may be configured to exchange data in the wireless-network 10120 with the computing device 10118 via a networking device intermediary such as a wireless router or gateway, or other networking device. The communications module 998 may be configured to exchange data in the wireless-network 10120 directly with the computing device 10118 such as in a peer-to-peer configuration. In some examples, the communications module 998 may be selectively configured to exchange data with the computing device 10118 via a networking device intermediary and/or peer-to-peer. Sensitive patient data such as patient health information may be encrypted as it is stored on the medical drain device 100, such as on either of the memories 9102, 9110. In case of the patient health information being transferred with the communications module 998, a secure connection or encryption is used to protect the data. To further protect the patient health data, data stored in the medical drain device 100 may be deleted after it is successfully transferred with the communications module 998. In one example, the communications module 998 may transfer the data, and then receive a confirmation from the computing device 10118 via protocol that the data was successfully received. After receiving confirmation, the communications module 998 may initiate the controller 996 and/or the microcontroller 9106 to begin a process of deleting the successfully transferred data. In one example, the process of deleting the successfully transferred data may be performed during periods of low sensor activity, periods of high power source capacity, or some other preferred period to reduce processing power of the controller 996 or improve power source capacity. The secured or encrypted patient data can be transferred again from the computing device 10118 to the remote server 10122. Once the data has been successfully transferred to the remote server 10122 from the computing device 10118, the data may be erased from the computing device 10118 or the medical drain device 100 in a similar manner as deleting the data from the medical drain device 100.

It is contemplated that the computing device 10118 may be replaced with a networking device intermediary such as a wireless router, a gateway, or any other communications device.

The second computing device 10126 may be provided with one or more computer programs, such as computer programs specifically configured for a patient 102 or the caregiver, computer programs specifically configured for clinicians, computer programs specifically configured for researchers, or other programs. In one example, the computer programs may be configured to receive patient data and data responsive to the sensed flow pressure signals. In another example, a computer program may be configured to receive telemetry data related to operation of the systems and applications of the medical drain device 100 and not related to patient data. The computer program may be a browser-based application. The computer program may be configured to present data from the communications module 998 in a form that is usable by the patient 102 or the caregiver, such as on a user interface that presents relevant data to the patient 102 or the caregiver. Also, via the user interface of the second computing device 10126, the patient 102 or the caregiver may interact with the medical drain device 100, such as by controlling the flow regulator 112.

Although the communications system 10116 has been described as having a remote server 10122, it is contemplated that the remote server 10122 may be omitted and at least one of the computing device 10118 and the second computing device 10126 may encompass the remote server's 10122 functionality.

An example method for managing patient fluid drain using the medical drain device of FIG. 1 is described below. The medical drain device 100 is provided and assembled as shown in FIG. 1 with the reservoir 178 connected to the reservoir connector 184. The drain inlet 104 is then placed in or adjacent to a wound or surgical site of the patient 102. Negative pressure is actively or passively provided in the medical drain device 100 to draw fluids from the wound or surgical site into the medical drain device 100 for draining.

Figure 11:
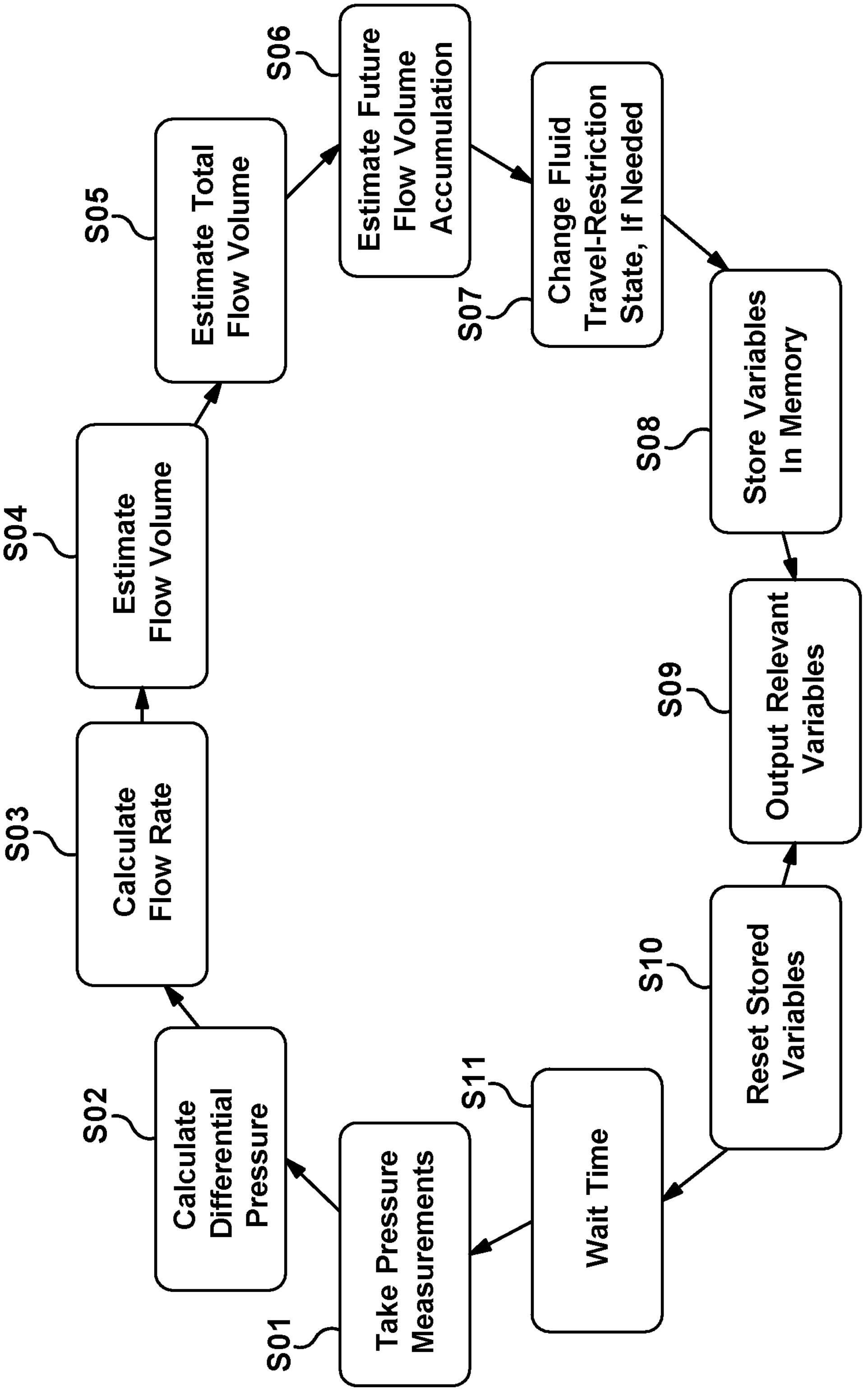
FIG. 11 is a flow diagram illustrating an example sequence of operation for managing patient fluid drain.

As shown in FIG. 11, in step S01, after a predetermined period of time has passed, the first pressure sensor 556 senses a first flow pressure in the inner housing chamber 452 adjacent the first connector port 464, while the second pressure sensor 558 senses a second flow pressure in the inner housing chamber 452 adjacent the second connector port 466. These measurements taken by the first and second pressure sensors 556, 558 may be taken after a desired period of time passes after the start of the fluid drain, after a desired amount of fluid has entered the medical drain device 100, after a desired amount of fluid has drained into the reservoir 178, after being instructed to do so by the controller 996, and/or responsive to any other stimulation, temporal, or other type of trigger. The first pressure sensor 556 produces and transmits a first flow pressure signal responsive to the sensed first flow pressure. Similarly, the second pressure sensor 558 produces and transmits a second flow pressure signal responsive to the sensed first flow pressure.

The processor 9100 receives the first and second pressure signals from the first and second pressure sensors 556, 558. The processor 9100 may receive these signals via a wireless or wired communication. For example, the communications module 998 may receive the first and second pressure signals and then provide them to the processor 9100. Alternatively, the processor 9100 may be in direct wired or wireless communication with the first and second pressure sensors 556, 558 for directly receiving the first and second pressure signals. The received first and second pressure signals include relevant information such as, for example, the sensed first and second flow pressures and, optionally, the time those measurements were taken. In step S02, the processor 9100 determines a differential pressure between the first and second flow pressures from the received first and second flow pressure signals.

In step S03, the processor 9100 determines a flow rate responsive the determined differential pressure. The flow rate can be determined using the Hagen-Poiseuille equation below:

$$Q = \frac{\Delta P * \pi * r^4}{8 * \mu * L}$$

where "Q" is the flow rate, "AP" is the determined differential pressure, "r" is the radius of the inner housing chamber 452, "u" is the dynamic viscosity of the drained fluid, and "L" is the length of the inner housing chamber 452 between where the first and second flow pressures are measured.

In step S04, the processor 9100 then estimates a flow volume that has passed through the sensor system 442 as a function of the determined flow rate. The flow volume may be estimated using the following equation:

$$V = \frac{\Delta T}{2} * (Q + Q_{prev})$$

where "V" is the current estimated flow volume, "Q" is the flow rate determined in step S03, "$Q_{prev}$" is a previously determined flow rate from a previous cycle of the loop shown in FIG. 11, and "ΔT" is a time interval between when Q and $Q_{prev}$ are determined. With this equation, the processor 9100 uses a trapezoidal integral approximation to make an estimate of the total amount of fluid that passed through the sensor system 442 every time interval.

In step S05, the processer 9100 estimates a total amount of fluid (i.e., total flow volume) that has drained from the patient 102. The total flow volume may be estimated using the following equation:

$$V_{tot} = V + V_{tot\text{-}prev}$$

where "$V_{tot}$" is the current estimated total flow volume drained from the patient 102, "V" is the estimated flow volume from step S04, and "$V_{tot\text{-}prev}$" is a previously estimated $V_{tot}$ from a previous cycle of the loop shown in FIG. 11. Therefore, the $V_{tot}$ updates using a new flow volume estimate from step 04 during every cycle of the loop shown in FIG. 11.

In step S06, the processor 9100 estimates a future flow volume accumulation as a function of the estimated total flow volume and the determined flow rate, and compares the estimated future flow volume accumulation with a predetermined future flow volume accumulation. The predetermined future flow volume accumulation may be predetermined by the caregiver and stored in the memory 9102. The comparison in step S06 helps determine, for example, if an estimated current rate of fluid accumulation would, by the end of the day, result in the patient 102 exceeding a caregiver-specified daily max volume accumulation.

In step S07, if the processor 9100 determines that the estimated future flow volume accumulation is greater than the predetermined future flow volume accumulation, the controller 996 may instruct the flow regulator 112 to increase the level of fluid travel restriction in the medical drain device 100. For example, if the physician-specified daily max volume is estimated to be on track to be exceeded, then the fluid travel-restriction state may increase from 0% (which may be the default) to, for example, 50%. If, on the next cycle of the loop of FIG. 11, the fluid travel-restriction state is at 50%, and the estimated current rate of fluid accumulation is still expected to exceed the caregiver-specified daily max volume accumulation, then the fluid travel-restriction state may increase, for example, from 50% to 100%. Similarly, the fluid travel-restriction state may be decreased on a subsequent cycle if the estimated current rate of fluid accumulation (i.e., the estimated future flow volume accumulation) is expected to fall below the caregiver-specified daily max volume accumulation (i.e., the predetermined future flow volume accumulation). Furthermore, if the estimated future flow volume accumulation is less than the predetermined future flow volume accumulation on the first cycle or subsequent cycles, the fluid travel-restriction state may remain unchanged.

The controller 996 may be configured to notify the patient 102 or the caregiver of the fluid travel-restriction state during use of the medical drain device 100. Therefore, the patient 102 or the caregiver may be alerted when the fluid travel-restriction state changes, such as when the fluid travel-restriction state increases and at least a portion of fluid travel between the drain inlet and outlets 104, 180 is restricted via the flow regulator 112. The patient 102 or the caregiver may be alerted in any user-perceptible manner such as, but not limited to, via an indication light, a sound, and/or a message written on a display screen.

In step S08, a current device time and the current cycle's $\Delta P$, Q, and $V_{tot}$ variables may be stored on the memory 9102. Other received, determined, and/or estimated variables (e.g., the first flow pressure and the second flow pressure) may also be stored in the memory 9102.

In step S09, the controller 996, via the communications module 998 may output relevant parameters/variables to the computing device 10118 for use by the patient 102 or the caregiver. In order to transmit the relevant parameters, the processor 9100 may first produce indication signals responsive to the relevant parameters. For example, the processor 9100 may produce at least one of: a differential pressure indication signal responsive to the determined differential pressure from step S02; a first flow pressure indication signal responsive to the sensed first flow pressure from step S01; a second flow pressure indication signal responsive to the sensed second flow pressure from step S01; an average flow pressure indication signal responsive to the average of the first and second flow pressures, where the average flow pressure indication signal may correspond to a fluid pressure in the medical drain system; a flow rate indication signal responsive to the determined flow rate from step S03; a flow volume indication signal responsive to the estimated flow volume from step S04; a total flow volume indication signal responsive to the current estimated total flow volume from step S06; a future flow volume accumulation indication responsive to the estimated future flow volume accumulation from step S06; a predetermined future flow volume indication signal responsive to the caregiver-specified daily max volume accumulation; a fluid travel-restriction state responsive to the current state of the flow regulator 112 and from step S07; one or more timing indication signals responsive to the times in which any measurements are taken, determined, estimated, or processed, and any other desired indication signal or combination of indication signals. One or more of these indication signals may be stored in at least the memory 9102 before being transmitted out.

Any number of indication signals may be transmitted to the computing device 10118, to the remote server 10122 via the computing device 10118, and/or to the second computing device 10126 via the computing device 10118 and/or the remote server 10122 for use by the patient 102 or the caregiver. Alternatively or additionally, the indication signals may be transmitted to a user-perceptible display screen of the medical drain device 100 for notifying the patient 102 or the caregiver of the relevant parameters. The transmitted indication signals may be presented to the patient 102 or the caregiver in a user perceptible manner. Based on at least one of the presented parameters from at least one of the indication signals, the patient 102 or the caregiver may interact with the medical drain device 100. For example, based on one or more of the presented parameters, the patient 102 or the caregiver, via the computing device 10118 or the second computing device 10126, may instruct the controller 996 to adjust the flow regulator 112 as desired.

In step S10, certain previously stored variables may be reset with currently determined or estimated variables. For example, the $V_{tot\text{-}prev}$ used in the present cycle may be reset with the current estimated total flow volume from step S05. The $Q_{prev}$ used in the present cycle may be reset with the current determined flow rate from step S03. A stored state of the flow travel-restriction may also be updated when changed in step S07 during a cycle of the loop. Variables/parameters that are no longer necessary at the end of a cycle of the loop may be deleted from the memory 9102.

In step S11, after a predetermined period of time passes (e.g., 15 seconds), the loop restarts at step S01. The loop can be cycled through throughout the entire use of the medical drain device 100 or as requested by the patient 102 or the caregiver.

It should be noted that the controller 996 may provide a notification or alert, via, for example, an indicator light, a sound, a written message, to the patient 102 or the caregiver to alert the patient 102 or the caregiver when certain parameters are outside a predetermined desirable range, when certain parameters are in predetermined states, and/or when certain components are in use, are malfunctioning, and/or are in predetermined use states. Certain notifications or alerts may be configured to resolve after a predetermined period of time, while other notifications or alerts may be configured to require patient/caregiver interaction to ensure that the alert was noticed by the patient/caregiver. In certain circumstances, the controller 996 may keep track of items that the controller 996 would typically alert or notify the patient 102 or caregiver of instead of alerting or notifying the patient 102 or caregiver. For example, the controller 996 may be configured to keep track of, but withhold alerts/notifications depending on the time of day, the degree of the issue/state causing the alert/notification, when requested to by the patient 102 or caregiver, for any other reason, or for any combination thereof.

It is contemplated that any electronic communication described herein as being made wirelessly could instead, or additionally, be made via a wired connection, and vice versa.

It is contemplated that the medical drain device 100 could include at least one of a filter, a measuring means (e.g., weight scale or tick-mark type scale), a sensor for sensing fluid color, a pressure or fluid release valve, one or more features for sensing the presence of a blockage and/or at least partially alleviating a blockage in the medical drain device 100, any other feature that may be desirable by the patient/caregiver before, during, or after use of the medical drain device 100, or any combination thereof.

It is contemplated that the medical drain device 100 may be portable such that it can be carried on the patient's body and configured to travel with the patient 102. For example, the medical drain device 100 can be worn on the patient's body and carried from location to location, including locations away from a medical care facility. In one example, the portable medical drain device 100 can continue to communicate with caregivers at a medical care facility when worn in remote locations.

Although the medical drain device 100 has been described as being for medical purposes with a patient, the medical drain device 100 may be configured to be applicable in fields outside the field of medicine.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A method for managing patient fluid drain, the method comprising:

providing a medical drain device, the medical device including a drain inlet for receiving fluid flow from a patient, a drain outlet for releasing fluid flow to a reservoir, a sensor system interposed fluidically between the drain inlet and the drain outlet, the sensor system comprising first and second pressure sensors, the sensor system producing a sensed flow pressure signal responsive to fluid travel between the drain inlet and the drain outlet, a flow regulator interposed fluidically between the drain inlet and the drain outlet and being configured to selectively restrict at least a portion of fluid travel between the drain inlet and the drain outlet, and a controller configured to receive the sensed flow pressure signal and responsively produce at least one of a flow rate indication signal, a flow pressure indication signal, and a flow volume indication signal;

sensing a first flow pressure in the medical drain device with the first pressure sensor;

producing and transmitting a first flow pressure signal responsive to the first flow pressure with the first pressure sensor;

sensing a second flow pressure in the medical drain device with the second pressure sensor;

producing and transmitting a second flow pressure signal responsive to the second flow pressure with the second pressure sensor;

receiving the first and second sensed flow pressure signals at the processor;

determining a differential pressure between the first and second flow pressures from the received first and second sensed flow pressure signals with the processor;

determining a flow rate responsive to the determined differential pressure with the processor;

estimating a flow volume that has been drained from the patient as a function of the determined flow rate with the processor;

estimating a future flow volume accumulation as a function of the estimated flow volume and determined flow rate with the processor;

comparing the estimated future flow volume accumulation with a predetermined future flow volume accumulation with the processor; and restricting at least a portion of fluid travel between the drain inlet and the drain outlet with the flow regulator if the estimated future flow volume accumulation is greater than the predetermined future flow volume accumulation.

2. The method of claim 1, further comprising:

producing a user-perceptible alert when the estimated future flow volume accumulation is greater than the predetermined future flow volume accumulation, and/or when the flow regulator restricts at least a portion of the fluid travel between the drain inlet and the drain outlet.

* * * * *